United States Patent
Meythaler

(10) Patent No.: US 9,192,672 B2
(45) Date of Patent: Nov. 24, 2015

(54) ZWITTERION SOLUTION FOR LOW-VOLUME THERAPEUTIC DELIVERY

(71) Applicant: Wayne State University Board of Governors, Detroit, MI (US)

(72) Inventor: Jay M. Meythaler, Grosse Pointe Farms, MI (US)

(73) Assignee: Wayne State University Board of Governors, Detroit, MI (US)

( * ) Notice: Subject to any disclaimer, the term of this patent is extended or adjusted under 35 U.S.C. 154(b) by 97 days.

(21) Appl. No.: 13/750,566

(22) Filed: Jan. 25, 2013

(65) Prior Publication Data

US 2013/0137670 A1 May 30, 2013

Related U.S. Application Data

(62) Division of application No. 12/664,507, filed as application No. PCT/US2008/066855 on Jun. 13, 2008, now abandoned.

(60) Provisional application No. 60/943,732, filed on Jun. 13, 2007.

(51) Int. Cl.
*A61K 31/545* (2006.01)
*A61K 47/02* (2006.01)
*A61K 9/00* (2006.01)

(52) U.S. Cl.
CPC .............. *A61K 47/02* (2013.01); *A61K 9/0085* (2013.01)

(58) Field of Classification Search
None
See application file for complete search history.

(56) References Cited

U.S. PATENT DOCUMENTS

| | | |
|---|---|---|
| 4,313,945 A | 2/1982 | Wiederkehr et al. |
| 4,443,440 A | 4/1984 | Anderson et al. |
| 4,467,101 A | 8/1984 | Kocsis et al. |
| 4,493,832 A | 1/1985 | Teraji et al. |
| 4,515,960 A | 5/1985 | Teetz |
| 4,539,161 A | 9/1985 | Guglielmetti |
| 4,727,160 A | 2/1988 | Teetz et al. |
| 4,735,937 A | 4/1988 | Heusler et al. |
| 4,855,290 A | 8/1989 | Fisher et al. |
| 4,971,962 A | 11/1990 | Oh et al. |
| 5,061,722 A | 10/1991 | Teetz et al. |
| 5,073,539 A | 12/1991 | Mazzenga et al. |
| 5,106,627 A | 4/1992 | Aebischer et al. |
| 5,149,713 A | 9/1992 | Bousquet |
| 5,583,218 A | 12/1996 | Takemura et al. |
| 5,935,795 A * | 8/1999 | Lin et al. ......................... 435/7.1 |
| 5,942,508 A | 8/1999 | Sawa |
| 5,994,365 A | 11/1999 | Zaworotko et al. |
| 6,028,223 A | 2/2000 | Ruminski et al. |
| 6,252,075 B1 | 6/2001 | Shiragami et al. |
| 6,500,809 B1 | 12/2002 | Frazer |
| 6,548,555 B1 | 4/2003 | Curatolo et al. |
| 6,656,172 B1 | 12/2003 | Hildebrand |
| 6,831,199 B1 | 12/2004 | Ruminski et al. |
| 6,969,383 B2 | 11/2005 | Hildebrand |
| 7,175,856 B2 | 2/2007 | Ullah et al. |
| 7,199,247 B2 | 4/2007 | Lemmens et al. |
| 2006/0009523 A1 | 1/2006 | Trissel et al. |
| 2011/0021469 A1 | 1/2011 | Meythaler et al. |

FOREIGN PATENT DOCUMENTS

WO WO-2008157288 12/2008

OTHER PUBLICATIONS

Clara (J Antimicrob Chemotherap 17:263-265; 1986).*
Famularo et al (Scandinavian J Gastroenterol 40:607-609, 2005).*
Oka et al, The significance of artificial cerebrospinal fluid as perfusate and endoneurosurgery, Neurosugery, 1996, 733-736, 38.
Griffith, Endoneurosurgery: endoscopic intracranial surgery, Advances in Technical Standards in Neurosurgery, 1986, 2-24, vol. 14, New York: Springer-Verlag, Symon L ed.
Griffith et al, The treatment of childhood hydrocephalus by choroid plexus coagulation and artificial cerebrospinal fluid perfusion, British Journal of Neurosurgery, 1990, 95-100, 4.
Jackson et al, A ?-aminobutyric acid agonist reverses the negative feedback effect of testosterone on gonadotropin-releasing hormone and luteinizing hormone secretion in the male sheep body, Endocrinology, 2000, 3940-3945, 141.
Goda et al, Simple and sensitive liquid chromatography-tandem mass spectrometry method for determination of the S(+) and R(-)-enantiomers of baclofen in human plasma and cerebrospinal fluid, J. Chromatogr. B Analyt. Technol. Biomed. Life Sci., 2004, 257-64, 801.
Winslow et al, New transfusion strategies: red cell substitutes, Annual Review of Medicine, 1999, 337-353, 50.
Ross et al, Aqueous solubilities of some variously substituted quinolone antimicrobials, Intl. J. Pharm., 1990, 237-250, 63.
Lagarce et al, Baclofen-loaded microspheres in gel suspensions for intrathecal drug delivery: in vitro and in vivo evaluation, Eur J Pharm Biopharm, 2005, 171-80, 61.
Sitaram et al, Stability and compatibility of baclofen and morphine admixtures for use in an implantable infusion pump, Int J Pharm, 1997, 13-24, 153.
Gupta et al, Quantitation of 4-(4-chlorophenyl)-2-pyrrolidine in baclofen powder and tablets, Drug Develop Indust Pharm, 1998, 1623-1628, 14.
Johnson et al, Stability of an extemporaneously compounded baclofen oral liquid, Am J Hosp Pharm, 1993, 2353-55, 50.
Allen et al, Stability of baclofen, captopril, diltiazem hydrochloride, dipyridamole, and flecainide acetate in extemporaneously compounded oral liquid, Am J Health-Syst Pharm, 1996, 2179-2184, 53.

(Continued)

*Primary Examiner* — Craig Ricci
(74) *Attorney, Agent, or Firm* — Dinsmore & Shohl LLP

(57) ABSTRACT

A formulation is provided that includes a volume of an aqueous multivalent physiological ion solution compatible with cerebrospinal fluid containing at least one divalent cation of magnesium or calcium, and at least one anion of carbonate or phosphate, and having a pH between 6.5 and 8.0. A zwitterionic therapeutic agent other than baclofen is dissolved the solution to achieve higher concentration or ease of solution and/or storage relative to therapeutic saline solutions of the same agent. A process of delivering a zwitterionic therapeutic agent into a subject is provided that includes dissolving a therapeutic amount of the zwitterionic therapeutic agent in a volume of artificial cerebrospinal fluid to form a stable formulation. The solution is then administered to the subject using an intrathecal pump.

2 Claims, No Drawings

(56) References Cited

OTHER PUBLICATIONS

Samson-Fang, L. et al., Intrathecal baclofen withdrawal simulating neuroleptic malignant syndrome in a child with cerebral palsy, Developmental Medicine & Child Neurology, 42(8): 561-65, 2000.

Berning, S. et al., Novel Treatment of Meningitis Caused by Multidrug-Resistant *Mycobacterium tuberculosis* with Intrathecal Levofloxacin and Amikacin: Case Report, Clinical Infectious Diseases, 32:643-46, 2001.

Fishman, R., Cerebrospinal Fluid in Disease of the Nervous System, 1980 (based on faculty.washington.edu/chudler/facts.html).

Schmuck, G. et al., Determination of the Excitatory Potencies of Fluoroquinolones in the Central Nervous System by an in Vitro Model, Antimicrobial Agents and Chemotherapy, 42(7): 1831-36, Jul. 1998.

Walwaikar, P. et al., Ofloxacin in multidrug resistant tuberculosis, J. Indian Med Assoc, 101(3): 210-12, Mar. 2003 (Abstract only).

Won, S. et al., Influence of age on the response to fibroblast growth factor-2 treatment in a rate model of stroke, Brain Research, 1123: 237-44, Oct. 24, 2006.

Information for Healthcare Professions: Ceftrixone (marketed as Rocephin and generics), issued by the U.S. Food and Drug Administration, Apr. 21, 2009 (accessed Apr. 18, 2015).

RxList, The Internet Drug Index, Patient Information, Rocephin (Ceftriaxone) Drug Information: Indications, Dosage and How Supplied, Apr. 6, 2015.

\* cited by examiner

US 9,192,672 B2

ZWITTERION SOLUTION FOR LOW-VOLUME THERAPEUTIC DELIVERY

CROSS REFERENCE TO RELATED APPLICATIONS

This application is a divisional of U.S. patent application Ser. No. 12/664,507, which is a U.S. national stage application of PCT/US2008/066855, filed Jun. 13, 2008, which claims priority from U.S. Provisional. Application Ser. No. 60/943,732, filed on Jun. 13, 2007, the entire content of all of which are incorporated herein by reference as if explicitly stated herein.

FIELD OF THE INVENTION

The invention relates to the field of high concentration therapeutic zwitterion solutions in cerebrospinal fluid compatible solution suitable for clinical and research intrathecal administration, more particular, in an artificial cerebrospinal fluid solution, and medical package suitable for clinical delivery to patients and use in medical devices designed to deliver solution based the therapeutic zwitterions to patients.

BACKGROUND OF THE INVENTION

A zwitterion is a chemical compound that is electrically neutral through a net cancellation of formal positive and negative charges within the compound. Zwitterions are polar and usually have a higher solubility at acid and basic pH values where a net charge exists in the compound. However, at physiologic pH a net zero charge often reduces solubility. This phenomenon is utilized in isoelastic focusing techniques with pH graded media.

Some zwitterions are useful medical therapeutics. Unfortunately, the low solubility of zwitterionic compounds at physiological pH has resulted in low dose high volume administration that limits the pharmokinetics of the agent. Alternatively, the zwitterion is functionalized to increase solubility, but usually at the expense of physiological activity.

In attempting to develop effective modes of administration that are likely to enhance patient compliance, spinal injection has been recognized as an attractive site where a localized therapy in the neuronal area of a patient is necessary. The use of directed intrathecal administration of zwitterionic compound either by bolus injection or by infusion regulated by refillable, implantable pump systems has drastically improved clinical feasibility of administration. Here as well, poor solubility of the zwitterionic therapeutic agent in saline solution necessitates multiple intrathecal pumping cycles to achieve an efficacious dose. Furthermore, when additional modulators are to be combined with the zwitterionic therapeutic agent, the levels of the zwitterionic therapeutic agent dissolvable in the saline solution are reduced.

By way of example, a zwitterionic compound usage as a therapeutic, baclofen, is indicated as a muscle relaxant and antispastic, in aqueous solutions has been extensively investigated. A theoretical upper limit of baclofen solubility is estimated to be 4.3 mg/ml. This is achieved through weeks' or months' dissolution of powder baclofen. The resulting suspension, however, is not suitable for intrathecal delivery. Increased solubility has been achieved in aqueous saline solution to as high as 12 mg/ml through extreme heating at 100° Celsius, intense agitation such as sonication, and high speed stirring. U.S. Patent Application Publication 2006/0009523. The drawbacks of this method are that it is time consuming and requires instrumentation not commonly found in a clinical setting. Another method that has shown some success is by initial dissolution in acid solution with pH levels below 3.87. Just prior to administration a base is added to bring the pH to pharmaceutically acceptable levels. This back titration method produces baclofen concentrations of nearly 10 mg/ml. U.S. Patent Application Publication 2006/0009523. The back titration method, however, required the use of strong acids or bases for the initial baclofen salvation that persist as a component of the clinically delivered baclofen solution. Further, saline solutions suffer neurotoxic complications resulting from their differing pH, osmotic pressure, membrane-active ion concentration, and $CO_2$. Oka, K, et al., *Neurosurgery*, 1996; 38:733-736; Griffith H B: *Endoneurosurgery: Endoscopic intracranial surgery*, in Symon L (ed): Advances and Technical Standards in Neurosurgery. Wien, Springer-Verlag, 1986; 4:2-24; Griffith, H B, and Jamjoom A B, *Br J Neurosurg*, 1990; 4:95-100.

An alternative to saline or other aqueous solution for baclofen administration is artificial cerebrospinal fluid (aCSF). Differing forms of aCSF were previously used for in vivo pharmacological studies of baclofen administration. Jackson, G L, et al., *Endocrinology*, 2000; 141: 3940-3945; Goda, R. et al., *J Chromatogr B Analyt Technol Biomed Life Sci*, 2004; 801:257-64. However, the baclofen concentrations achieved in these and other studies were less than 0.21 mg/ml.

Similar to baclofen, a variety of therapeutics have indications for cerebrospinal administration are also zwitterions at physiological pH. These therapeutic zwitterions have a variety of activities inclusive of neurotransmitter agonists and antagonists, antibiotics, anti-inflammatories, psychotropics, and neurotransmitter mimics. As with baclofen, the poor solubility of these therapeutic zwitterions has limited therapeutic efficacy owing to the large carrier volumes needed to solubilize needed doses.

Thus, there exists a need for a formulation whereby the solubility of a zwitterionic therapeutic agent is increased relative to conventional techniques. There further exists a need for a high concentration zwitterionic therapeutic agent that is amenable to storage and delivery by common routes such as intravenous, intramuscular and intrathecal.

SUMMARY OF THE INVENTION

A formulation is provided that includes a volume of an aqueous multivalent physiological ion solution compatible with cerebrospinal fluid containing at least one divalent cation of magnesium or calcium, and at least one anion of carbonate or phosphate, and having a pH between 6.5 and 8.0. A zwitterionic therapeutic agent other than baclofen is dissolved the solution to achieve higher concentration or ease of solution and/or storage relative to therapeutic saline solutions of the same agent. A specific aqueous multivalent physiological ion solution contains 130-160 mM NaCl, 2.7-3.9 mM KCl, 1-3 mM $CaCl_2.2H_2O$, 0.5-2.5 mM $MgCl_2.6H_2O$, 0.5-1.0 mM $Na_2HPO_4.7H_2O$, 0.1-0.5 mM $NaH_2PO_4H_2O$, and has a pH between 6.5 and 8.0. Specific zwitterionic therapeutic agents operative herein include salicylates, fexofenadine, ofloxacin, cefepine, (4-{2-[2-hydroxy-2-(2-trifluoromethyl-thiazol-4-yl)-ethylamino]-propyl}-phenoxy)-acetic acid, 7-(6-amino-3-aza-bicyclo[3.1.0]hex-3-yl)-1-(2,4-difluorophenyl)-6-fluoro-4-oxo-1,4-dihydro-[1,8]naphthyridine-3-carboxylic acid, 1-cyclopropyl-8-(difluoromethoxy)-7-[(1R)-1-methyl-2,3-dihydro-1H-5-isoind-olyl]-4-oxo-1,4-dihydro-3-quinolinecarboxylic acid methanesulfonate monohydrate (bis-quinolone), (Z)-4-[(2-{[4-(2-chlorophenyl)-3-(ethoxycarbonyl)-5-(methoxycarbonyl)-6-methyl-1,4-dihydro-2-pyridinyl]methoxy}ethyl)amino]-4-oxo-2- butenoic acid, cis, endo-2-azabicyclo-[3.3.0]-octane-3-carboxylic acids, cephalosporin, cefdinir, cefixime, cefpodoxime, ceftriaxone, 2-azabicyclo-[3.3.0]-octane-3-carboxylic acids, spiro-2-aza-alkane-3-carbonitriles heterocylic selenates of the formulae

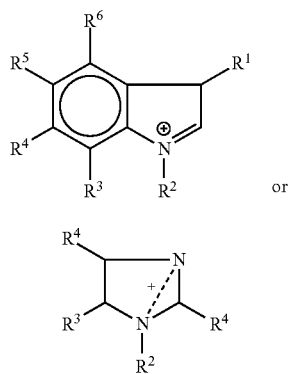

where $R^1$, $R^2$, $R^3$, $R^4$, $R^5$ and $R^6$ are each independently hydrogen, $C_1$-$C_6$ alkyl, a $C_0$-$C_6$ alkyl having a substituent of amine or hydroxyl, and a $C_0$-$C_{16}$ selenol with the proviso that one and only one of $R^1$-$R^6$ contains a SeH moiety.

A process of delivering a zwitterionic therapeutic agent into a subject is provided that includes dissolving a therapeutic amount of the zwitterionic therapeutic agent in a volume of artificial cerebrospinal fluid to form a stable formulation. The solution is then administered to the subject using an intrathecal pump.

DETAILED DESCRIPTION OF THE PREFERRED EMBODIMENTS

The present invention has utility as a zwitterionic therapeutic agent solution. The present invention allows for higher concentrations of zwitterionic therapeutic agent to be administered to patients so as to increase the likelihood of clinical benefit, simplify administration logistics and allow for the optional simultaneous administration of other therapeutics.

The present invention relates to a solution of zwitterionic therapeutic agent dissolved in a multivalent physiologic ion (MPI) solution that includes at least one divalent cation of magnesium or calcium, and at least one anion of carbonate or phosphate of a pH between 6 and 8.5. The resulting formulation achieves higher concentrations of the zwitterionic therapeutic agent relative to saline solutions. A MPI solution of the present invention simulative of cerebrospinal fluid preferably includes 130-160 mM NaCl, 2.7-3.9 mM KCl, 1-3 mM $CaCl_2 \cdot 2H_2O$, 0.5-2.5 mM $MgCl_2 \cdot 6H_2O$, 0.5-1.0 mM $Na_2HPO_4 \cdot 7H_2O$, 0.1-0.5 mM $NaH_2PO_4 \cdot H_2O$. In instances where the zwitterionic therapeutic agent is provided intrathecally, the MPI solution is artificial cerebral spinal fluid containing 148 mM NaCl, 3 mM KCl, 1.4 mM $CaCl_2 \cdot 2H_2O$, 0.8 mM $MgCl_2 \cdot 6H_2O$, 0.8 mM $Na_2HPO_4 \cdot 7H_2O$, and 0.2 mM $NaH_2PO_4 \cdot H_2O$.

The present invention also provides a process for administering an amount of zwitterionic therapeutic agent in a reduced volume using an intrathecal pump. The process also optionally includes concurrent administration of medical modulators such as pain killer and inflammation-control reagents.

As used herein, a "subject" is defined as a mammal and illustratively includes non-human primates, horses, goats, cows, sheep, pigs, dogs, cats, and rodents. A human subject is also considered to benefit from the present invention. The methods and compounds of the present invention are administered in therapeutically effective amounts.

As used herein, a "therapeutically effective amount" is defined to include an amount necessary to delay the onset of, inhibit the progress of, relieve the symptoms of, or reverse a condition being treated. The therapeutically effective amount is one that is less than that that produces medically unacceptable side effects. It is appreciated that a therapeutically effective amount varies with a number of factors illustratively including subject age, condition, sex and the nature of the condition being treated. It is further appreciated that determining a therapeutically effective dose is within the knowledge of one of ordinary skill in the art.

Common but not exclusive features of a zwitterionic therapeutic agent are offsetting positive and negative charges at physiological pH associated with cerebrospinal fluid (CSF) or blood and a monomeric molecular weight of less than 2,000 Daltons. Dimeric or higher oligomers of conjugated zwitterionic therapeutic agents that exceed the molecular weight of 2,000 Daltons are considered to be operative herein.

Therapeutic zwitterionic agents operative herein illustratively include: salicylates, such as choline-magnesium salicylate; fexofenadine; ofloxacin; cefepine; (4-{2-[2-hydroxy-2-(2-trifluoromethyl-thiazol-4-yl)-ethylamino]-propyl}-phenoxy)-acetic acid per U.S. Pat. No. 6,548,555; 7-(6-amino-3-aza-bicyclo[3.1.0]hex-3-yl)-1-(2,4-difluoro-phenyl)-6-fluoro-4-oxo-1,4-dihydro-[1,8]naphthyridine-3-carboxylic acid per U.S. Pat. No. 6,548,555; cyclopropyl-8-(difluoromethoxy)-7-[(1R)-1-methyl-2,3-dihydro-1H-5-isoind-olyl]-4-oxo-1,4-dihydro-3-quinolinecarboxylic acid methanesulfonate monohydrate (bis-quinolone) per U.S. Pat. No. 7,175,856; (Z)-4-[(2-{[4-(2-chlorophenyl)-3-(ethoxy-carbonyl)-5-(methoxycarbonyl)-6-methyl-1,4-dihydro-2-pyridinyl]methoxy}ethyl)amino]-4-oxo-2-butenoic acid per U.S. Pat. No. 7,199,247; cis, endo-2-azabicyclo-[3.3.0]-octane-3-carboxylic acids per U.S. Pat. No. 5,061,722; cephalosporin; cefdinir; cefixime; cefpodoxime; ceftriaxone; 2-azabicyclo-[3.3.0]-octane-3-carboxylic acids per U.S. Pat. No. 4,727,160; piro-2-aza-alkane-3-carbonitriles per U.S. Pat. No. 4,515,960; heterocylic selenates of the formulae

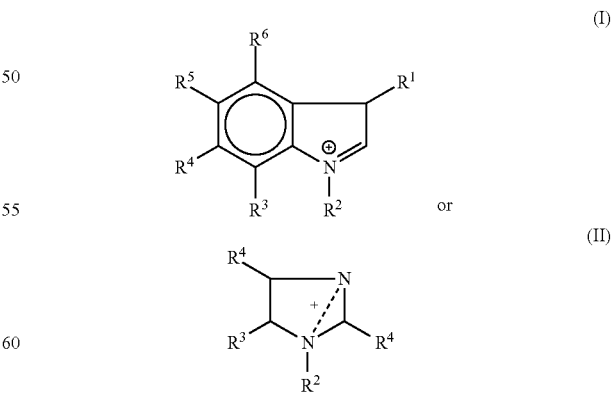

where $R^1$, $R^2$, $R^3$, $R^4$, $R^5$ and $R^6$ are each independently hydrogen, $C_1$-$C_6$ alkyl, a $C_0$-$C_6$ alkyl having a substituent of amine or hydroxyl, and a $C_0$-$C_{16}$ selenol with the proviso that one and only one of $R^1$-$R^6$ contains a selenol (—SeH) moiety.

While not intending to be bound by a particular theory, at physiological pH selenol exists as selenate (—Se$^-$) while support of positive structure by the heterocyclic nitrogen or nitrogens of Formulae I or II renders these compounds zwitterionic. The compounds of formula I represent neuroactive compound mimics. By way of example, in Formula I when $R^5$ is —OH, $R^1$ is (CH$_2$)$_2$—NH$_2$, one of $R^2$, $R^3$, $R^4$ and $R^6$ is a $C_0$-$C_{16}$ selenol with the remainder of $R^2$, $R^3$, $R^4$ and $R^6$ being H represents a serotonin mimic. Serotonin is a well known neurotransmitter involved in learning, memory, depression and feeding behavior. Likewise, zwitterionic analogs of many naturally occurring alkaloids having neural activity based around the indole nucleus of Formula I are provided such as Harmaline, Cinchera, Yohimbine, Rauwolfia and Ergot alkaloids.

The base compounds of Formula II absent selenol have shown efficacy against various cancers (PubChem 210285, National Cancer Institute 146816).

Zwitterionic therapeutic agents other than those of Formulae I and II are operative herein.

It is appreciated that multicationic-multianionic zwitterionic therapeutic agents are readily administered by the present invention. Dimers, multimers and oligomers of any of the aforementioned zwitterionic therapeutic agents are readily formed by derivitizing a zwitterionic therapeutic agent to include a moiety capable of reaction to join at least two zwitterionic therapeutic agents so long as the zwitterionic moieties of the monomeric zwitterionic therapeutic agent are retained. Condensation reactions are particularly preferred in forming dimeric or higher order zwitterionic therapeutic agents. These dimeric or higher order zwitterionic therapeutic agents have different diffusion constants and metabolic clearance rates as compared to the monomeric form after administration. Typically the diffusion constants and metabolic clearance rates are lower for dimeric and higher order forms. These properties afford a variety of dosing options with the higher concentration solutions of the present invention and are considered to be zwitterionic therapeutic agents as the term is used with respect to the present invention.

A multivalent physiologic ion (MPI) solution of the present invention includes at least one divalent cation of magnesium or calcium, and at least one anion of carbonate or phosphate of a pH between 6 and 8.5. Other physiological ions such as sodium, potassium, onium and chloride are optionally provided. Preferably the MPI solution is within 30% of isotonicity with cerebrospinal fluid. An MPI solution also optionally includes an additive, the additive illustratively including glucose, oncotic agents, plasma extenders, and oxygen carrying components. The identity of such additives is further detailed below. Optionally, the inventive MPI zwitterionic therapeutic agent solution is saturated with 95% oxygen and 5% carbon dioxide to mimic the host physiologic gas concentration. Most preferably, an inventive MPI solution is based on artificial cerebrospinal fluid (aCSF).

The MPI solution is composed generally of physiological ions in a carbonate or phosphate buffered solution. This solution illustratively contains 130-160 mM NaCl; 2.7-3.9 mM KCl; 1-3 mM CaCl$_2$.2H$_2$O; 0.5-2.5 mM MgCl$_2$.6H$_2$O; 0.5-1.0 mM Na$_2$HPO$_4$.7H$_2$O; 0.1-0.5 mM NaH$_2$PO$_4$H$_2$O.

An inventive MPI based on aCSF contains 148 mM NaCl; 3 mM KCl; 1.4 mM CaCl$_2$.2H$_2$O; 0.8 mM MgCl$_2$.6H$_2$O; 0.8 mM Na$_2$HPO$_4$.7H$_2$O; and 0.2 mM NaH$_2$PO$_4$.H$_2$O. Additional or alternative components of aCSF are illustratively 20-25 mM sodium carbonate, 0.5-1.5 mM glucose, 200-450 mg/ml oncotic agent, or 5-20% oxygen carrying component. U.S. Pat. No. 6,500,809. Oncotic agents are illustratively proteins naturally found in plasma (e.g. the albumin, globulin, and fibrinogen fractions), mixtures of such proteins derived from human blood plasma (commonly called plasma protein fraction), plasma extenders such as the dextrans (glucose polymers of preferably 40,000 to about 80,000 average molecular weight) and starch 2-hydroxyethyl ether (sold as Hespan by DuPont), dextrins (cyclodextrin), carboxymethyl cellulose, polyethylene glycol, glycogen, and pluronic acid. Oxygen carrying components suitable in the instant invention include perfluorocarbon-based products, cell-free hemoglobin, and liposome encapsulated hemoglobin among others. Winslow, R M, *Annual Review of Medicine,* 1999; 50:337-353. Each of the above reagents are available by clinical or research suppliers known in the art. The pH of the above solutions is preferably at or between 5 and 8.

A preferred MPI solution contains: 124 mM NaCl, 3 mM KCl, 1.25 mM NaH$_2$PO$_4$, 1.2 mM MgSO$_4$, 26 mM NaHCO$_3$, 2 mM CaCl$_2$, and 10 mM dextrose.

Another preferred MPI solution contains 124 mM NaCl, 5 mM KCl, 1.3 mM MgCl$_2$, 2 mM CaCl$_2$, 26 mM NaHCO$_3$, and 10 mM D-glucose.

Rather than using conventional saline solution to dissolve a zwitterionic therapeutic agent an MPI solution, such as a CSF is used. Because a zwitterion is dipolar and hence charged, adding more ions increases solubility. It is appreciated that often a maximal concentration of zwitterionic therapeutic agent is achieved that subsequently sediments a portion of zwitterionic therapeutic agent to achieve a stable solution. As shown in Table 1, an increase in solubility of ceftriaxone is achieved by administration in artificial CSF as compared to conventional saline on zwitterionic therapeutic agent dissolution.

TABLE 1

|  | In Saline | In Artificial CSF |
| --- | --- | --- |
| Solubility of Ceftriaxone | 205 µg/ml | >250 µg/ml |

An inventive formulation through the use of an MPI solution serves to increase the final concentration of a zwitterionic therapeutic agent being administered to a subject relative to conventional saline solutions. Without intending to be bound to a particular theory, it is surmised that the inclusion of divalent ions of an MPI solution increase the size of the sphere of hydration around a zwitterionic therapeutic agent and in the process increase solubility. In contrast to prior art techniques to increase solubility of zwitterionic compounds through resort to sonication, heating, and vigorous agitation, zwitterionic therapeutic agents readily dissolve in an inventive MPI solution with no or nominal mechanical stirring. Furthermore, inventive formulations upon achieving equilibrium concentration are readily stored for later use. This attribute of an inventive formulation is in contrast to prior art efforts to increase zwitterionic therapeutic agent concentration that is strongly encouraged immediate administration as the higher concentrations so provided are unstable as detailed in U.S. Patent Application Publication 2006/0009533.

The instant invention also provides for a method of intrathecal delivery of the highly concentrated therapeutic zwitterion solution. An illustrative example of a pump system is that marketed under the trade name Accu-Check by Disetronic, Fishers, Ind. is operative as a delivery apparatus. The infusion pump is illustratively implantable, external, manual, or automatically regulated. Intravenous and intramuscular administration are also optionally practiced with an inventive formulation.

The formulations and processes of the invention are optionally used to treat mammalian patients (e.g., sport or pet mammals such as dogs, cats and horses, and humans). Additionally, the inventive compositions and methods are optionally used for, but are not limited to research purposes such as in clinical or preclinical in vivo animal studies involving mammals illustratively including mice, rats, guinea pigs, rabbits, dogs, cats, swine, bovine, monkey, baboon, chimpanzee, and humans.

The increased concentration of zwitterionic therapeutic agent achieved in the instant invention allows for subsequent dilution by the addition of other components that are simultaneously infused with the zwitterionic therapeutic agent. For instance spasticity, CSF inflammation, or infection are painful conditions and patients often require pain regulating medications. Pain regulating or relieving medications suitable for inclusion in an inventive zwitterionic therapeutic agent formulation are illustratively morphine, clondine, hydromorphine, hydrocodone, merperidine, celeroxib, tramadol, oxycodone, acetometaphen, ketaprofen, ibuprofen, naproxen sodium, and aspirin. It is appreciated in the art that other chemical compounds are similarly suitable for co-administration with a zwitterionic therapeutic agent in the instant invention.

In further embodiments, stable zwitterionic therapeutic agent solutions of the present invention are provided in a medical package of zwitterionic therapeutic agent solution illustratively suitable for injection, infusion, or other route of administration including oral. In a preferred embodiment the medical package contains a high concentration zwitterionic therapeutic agent in MPA solution and an optional second source of MPI solution diluent that is optionally used to adjust the dosing volume or concentration. The zwitterionic therapeutic agent solution is preferably provided free of pyrogens, antioxidants, preservatives or other potentially neurotoxic additives. In a particular package, the zwitterionic therapeutic agent solution and diluent are provided in single dose ampules. However, it is appreciated that a single ampule optionally contains partial or multiple dose volumes and concentrations. In a preferred embodiment the ampule is designed to operate in conjunction with an implantable pump and contains sufficient zwitterionic therapeutic agent solution such that continuous infusion may be maintained for three months or longer. Alternatively, the medical package is suitable for oral administration in liquid, tablet, powder, capsule, suspension, or other delivery form recognized in the art. In an alternative embodiment, the zwitterionic therapeutic agent solution is provided in a preloaded syringe that is suitable for manual injection or association with a syringe pump or other apparatus for longer infusion or injection times. Implantable infusion pumps generally designed for intrathecal zwitterionic therapeutic agent administration are commonly recharged by addition of additional therapeutic by injection into a reservoir in the pump. It is appreciated that the medical package of the instant invention is suitable for recharging both implantable and external pumps, as well as for direct delivery to the patient in the absence of a pump such as for initial test dosing of baclofen. Common medical packages for zwitterionic therapeutic agent are described in U.S. Patent Application Publication 2006/0009523. Preferably, a medical package includes instructions for the use thereof to treat a disease or injury The present invention is further detailed with respect to the following examples. These examples are not intended to limit the scope of the appended claims.

EXAMPLES

Example 1

Multivalent physiologic ion solution formation. A solution (A) is produced with 8.66 g NaCl, 0.224 g KCl, 0.206 g $CaCl_2.2H_2O$ and 0.163 g $MgCl_2.6H_2O$ dissolving in 500 mL of deionized water. A solution (B) is produced with 0.214 g $Na_2HPO_4.7H_2O$ and 0.027 g $NaH_2PO_4.H_2O$ dissolving in 450 mL of water. The pH is adjusted to 6.0, 6.5, 7.0, 7.3, 7.6 and 8.0 as necessary with either NaOH or $H_3PO_4$ and dilution to final volume of 500 mL with deionized water. A final multivalent physiologic ion solution is obtained by mixing equal parts of Solution A and B. pH is tested and adjusted to the desired final pH if necessary. All reagents are available from sources known in the art. Illustratively, reagents are available from Sigma-Aldrich Corp., St. Louis, Mo.

Example 2

Ofloxacin solubilization in multivalent physiologic ion solution. Ofloxacin powder, or ground tablets, are weighed and added to accurately measured volumes of MPI solution composed of 20 mM sodium carbonate, 8 mM $MgCl_2.6H_2O$, 5 mM $CaCl_2$, 150 mM NaCl titrated to pH 7.0. Solutions are warmed to 37° C. in a water bath. Each solution is manually mixed every minute during the first five minutes and at five minute intervals thereafter for an entire 30 minute aliquot pull period. Visually clear solutions are immediately obtained, but gentle stirring or vortexing is applied to the samples for several seconds to ensure complete solubilization of the ofloxacin. Clear solutions are achieved with no visual particulate matter remaining. Approximate 5 mL aliquots are pulled at 2, 5 and 30 minutes of incubation using a syringe equipped with a 10 micron filter tip. The aliquots are analyzed by high performance liquid chromatography (HPLC). For analyses, 2.0 mL of each aliquot is transferred to a 20 mL volumetric flask containing mobile phase. Additional linearity standards are optionally added. Ofloxacin concentrations of 5 mg/ml are achieved. In contrast, ofloxacin in PBS (saline) buffer has a solubility of only 3.23 mg/ml. Ross D. L. et al., Intl. J. Pharm. 1990; 63:237-250.

Example 3

Ofloxacin solubilization in artificial cerebrospinal fluid. Ofloxacin powder, or ground tablets, are weighed and added to accurately measured volumes of aCSF. Visually clear solutions are immediately obtained, but gentle stirring or vortexing is applied to the samples for several seconds to ensure complete solubilization of the ofloxacin. Ofloxacin concentrations are achieved in aCSF at 10 mg/ml. Solutions with greater than 7 mg/ml final concentrations required gentle agitation for 2 minutes or less. Clear solutions are achieved with no visual particulate matter remaining.

Example 4

Analyses of ofloxacin solutions to confirm concentrations. Ofloxacin concentrations of Examples 1 and 2 are determined to confirm soluble levels in aCSF in the inventive solutions. Ofloxacin concentrations are quantified by LC/MS/MS using an Applied Biosystems API 400 electrospray triple quadrupole mass spectrometer. Lagarce, F, et al., *Eur J Biopharm*, 2005, 61:171-80. Ofloxacin is separated on a $C_8$ 5 μm 100× 2.1 mm column in which the mobile phase is composed of 60% $H_2O$/40% acetonitrile at a solvent flow of 250 μl/min following a 20 µl sample injection. The transition between 214.1 and 151.2 is used for quantification. All samples are confirmed with less than 5% variation from expected values.

Example 5

Analyses of ofloxacin solutions to confirm concentrations. Alternatively, HPLC analyses of Examples 2 and 3 are used to confirm ofloxacin concentrations in the visually clear solution as described in U.S. Patent Application Publication 2006/0009523; Sitaram B R, et al., *Int J Pharm*, 1997; 153:13-24; Gupta V D, and Parasrampuria J, *Drug Develop Indust Pharm*, 1998; 14:1623-1628; Johnson C E, et al., *Am J Hosp Pharm*, 1993; 50:2353-55; Allen L V, et al., *Am J Health-Syst Pharm*, 1996; 53:2179-2184. Solutions are filtered through a 0.22-micron filter to remove any particulate matter. Ofloxacin is separated on a $C_{18}$ 5 µm 250×4.6 mm column with a mobile phase gradient of 0.085 M ammonium phosphate (78.5%) and acetonitrile (21.5%) to acetonitrile (100%) as previously described. Id. Detection was by UV at 220 nm.

Example 6

Administration of high concentration ofloxacin solution intrathecally. Patients presenting with head trauma and the presence of *E. coli* bacteria having entered the wound site who will have undergone subcutaneous placement of a programmable intrathecal ofloxacin pump (Medtronic SyncroMed Infusion System; Medtronic, Inc, Minneapolis, Minn.) are administered ofloxacin at appropriate dosage levels by intrathecal delivery. The inventive ofloxacin solution is optionally supplemented with a pain regulating medication such as morphine at appropriate dosage levels and is simultaneously loaded into the infusion pump for intrathecal delivery. Patients are monitored in the hospital for two to four days while dose is increased to achieve measurable bacterial load reduction without debilitating side effects.

Example 7

Administration of ofloxacin solution to mammals. Ofloxacin solution of Example 2 or 3 is administered to adult rats. Adult female rats of 250 g mean body weight and maintained under conditions of light on from 0700 h-1900 h, room temperature 23° C., water and food available ad libitum are ovarectomized and allowed to recover for two weeks. A stainless steel cannula is inserted. Following recovery of one week, rats are injected with flocci at 1 mg/ml in aCSF. Animals are studied for therapeutic and pharmacological effects of ofloxacin.

Alternatively, ofloxacin solution of Example 2 or 3 is administered to Wistar rat brain by superfusion. Briefly, a $0.4 \times 10^{-2}$ mg/ml solution of ofloxacin in aCSF is administered to anesthetized rats maintained to basic physiologic parameters of pH, $pO_2$, and $pCO_2$ by topical superfusion via an open cranial window prepared as described. Electrophysiological and other parameters are recorded prior to and following baclofen administration.

Administration of ofloxacin to cats. Cats weighing from 1.5 to 3.5 kg (n=4) are anaesthetized using pentobarbital (from 30 to 40 mg/kg administered first i.p., and then from 3 to 5 mg/kg administered i.v.) and then tracheotomised, curarised and ventilated artificially. The various basic haemodynamic parameters are recorded: arterial systolic and diastolic pressures, cardiac frequency, cardiac output. The various haemodynamic indices and parameters are also calculated (mean arterial pressure, dP/dt, double product frequency× pressure).

The core temperature of the animals is maintained at from 37° to 37.5° C. by means of an electric blanket. The animals are placed in a stereotactic apparatus and then the defense area is stimulated electrically by means of an electrode placed in the grey matter, at coordinates $A_6L_1H_0$. The stimuli are supplied by a stimulator functioning in monopolar manner: frequency 100 Hz, duration 3 msec., difference in potential 3 to 6 volts.

The positioning of the electrode is considered to be satisfactory when the cardiac output and dP/dt are increased by more than 20%.

The ofloxacin is administered via the femoral vein. The animals are given 0.5 mg/kg or 1 mg/kg as the case may be. The various parameters are then recorded 15 minutes and 30 minutes after the injection of ofloxacin.

Administration of ofloxacin and levofloxacin to calves. Healthy male crossbred calves (Holstein Friesian×Sahiwal), ranging between 1-1.5 years of age with an average body weight of 87.3±10.6 kg are maintained on seasonal green fodder, wheat straw and water ad libitum. Levofloxacin (Hoechst Marion Roussel, India) is administered intramuscularly at the dose rate of 4 mg/kg body weight into the neck region. Ofloxacin or levofloxacin (Hoechst Marion Roussel, India) solution in MPI is administered intramuscularly at the dose rate of 4-8 mg/kg body weight into the neck region. Blood samples (5 ml) are withdrawn from the jugular vein into heparinized glass centrifuge tubes and plasma is separated by centrifugation. Urine samples are simultaneously obtained. Measurement of plasma and urine concentration of drugs is performed by standard techniques. Dumka, V K and Srivastava, A K, *J. Vet. Sci.*, 2006; 7(4): 333-337.

Administration of ofloxacin to human patients with inflammatory central nervous system disorders. Patients are administered between 50 and 400 mg of ofloxacin in MPI or aCSF intravenously or intrathecally. Comedications administered include benzodiazepines, opioids, antibiotics, catecholamines, diuretics, antihypertensives, osmotherapeutics, corticosteroids, $H_2$-receptor blockers, morphine, clondine, hydromorphine, hydrocodone, merperidine, celeroxib, tramadol, oxycodone, acetometaphen, ketaprofen, ibuprofen, naproxen sodium, aspirin, and heparin according to clinical necessities. Patients are monitored in the hospital for two to four days for measurable bacterial load reduction without debilitating side effects.

Examples 8-14

The procedures of Examples 1-7 are repeated with ceftriaxone in place of ofloxacin. Ceftriaxone concentration in MPI solution of up to 700 µg/ml are readily obtained without aggressive dissolution techniques detailed in US 2006/0009523, and in excess of the 205 µg/ml solubility of ceftriaxone in saline. An indication of higher concentrations being obtainable exists. Similar detection techniques and methods are applicable to these ceftriaxone solutions.

Example 15

A person having ordinary skill in the art recognizes the experimental techniques applicable ofloxacin are similar to that of other zwitterionic compounds. Solubility results in either MPI or aCSF are increased in excess of 205 µg/ml for salicylates, fexofenadine, ofloxacin, cefepine, (4{2-[2-hydroxy-2-(2-trifluoromethyl-thiazol-4-yl)ethylamino]-propyl}-phenoxy)-acetic acid, 7-(6-amino-3-aza-bicyclo[3.1.O] hex-3-yl)-1-(2,4-difluoro-phenyl)-6-fluoro-4-oxo-1,4-dihydro-[1,8]naphthyridine-3-carboxylicacid, 1-cyclopropyl-8-(difluoromethoxy)-7-[(1R)-1-methyl-2,3-dihydro-1H-5-isoind-olyl]-4-oxo-1,4-dihydro-3-quinolinecarboxylic acid methanesulfonate monohydrate (bis-quinolone), (Z)-4-[(2-{[4-(2-chlorophenyl)-3-(ethoxycarbonyl)-5-(methoxycarbonyl)-6-methyl-1,4-dihydro-2-pyridinyl]methoxy}ethyl)amino]-4-oxo-2-butenoic acid, cis, endo-2-azabicyclo-[3.3.0]-octane-3-carboxylic acids, cephalosporin, cefdinir, cefixime, cefpodoxime, ceftriaxone, 2-azabicyclo-[3.3.0]-octane-3-carboxylic acids, spiro-2-aza-alkane-3-carbonitriles, or heterocylic selenates of the formulae I and 11 in either MPI or aCSF as determined by HPLC and LC/MS/MS as exemplified in Examples 4 and 5. Optimization of individual parameters for either HPLC or LC/MS/MS are within the skill or an ordinary practitioner of the art, are performed with regularity, and do not represent undue experimentation. Additionally, delivery of the inventive formulations to mammals, including humans, is within the skill or an ordinary practitioner of the art, performed with regularity, and do not represent undue experimentation. Each of these are evidenced by the above presented examples. Exemplary solubility of zwitterionic therapeutics in saline and aCSF are presented in Table 2.

TABLE 2

|  | In Saline | In Artificial CSF |
| --- | --- | --- |
| Solubility of Ceftriaxone | 205 µg/ml | >250 µg/ml |
| Solubility of ofloxacin | 3.23 mg/ml | >5 mg/ml |
| Solubility of fexofenadine | 0.6 mg/ml | >1 mg/ml |
| Solubility of cefixime | 55 µg/ml | >72 µg/ml |
| Solubility of cefixime | 68 µg/ml | >80 µg/ml |

TABLE 2-continued

|  | In Saline | In Artificial CSF |
| --- | --- | --- |
| Solubility of cephaprine | 1 mg/ml | >1.2 mg/ml |
| Solubility of cefepime | 66 µg/ml | >78 µg/ml |

Patent applications and publications mentioned in the specification are indicative of the levels of those skilled in the art to which the invention pertains. These applications and publications are incorporated herein by reference to the same extent as if each individual application or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A process of delivering ceftriaxone into a subject comprising:
    dissolving up to 700 µg/ml ceftriaxone in a volume of artificial cerebrospinal fluid comprising at least one divalent cation of calcium, said artificial cerebrospinal fluid comprising 130-160 mM NaCl, 2.7-3.9 mM KCl, up to 5 mM $CaCl_2.2H_2O$ 0.5-2.5 mM $MgCl_2.6H_2O$, and either 20-25 mM sodium carbonate or a combination of 0.5-1.0 mM $Na_7HPO_4.7H_7O$ and 0.1-0.5 mM $NaH_2PO_4.H_2O$, and having a pH between 6.5 and 8.0, to form a stable formulation with no particulate matter; and
    administering the formulation into the subject using an intrathecal pump.

2. The process of claim 1 further comprising a pain regulating agent.

* * * * *